US007494623B2

(12) United States Patent
Tansey, III

(10) Patent No.: US 7,494,623 B2
(45) Date of Patent: Feb. 24, 2009

(54) KINETIC MICROPLATE WITH REAGENT WELLS

(75) Inventor: Hugh H. Tansey, III, Southbury, CT (US)

(73) Assignee: Thermo Fisher Scientific (Asheville) LLC, Asheville, NC (US)

( * ) Notice: Subject to any disclaimer, the term of this patent is extended or adjusted under 35 U.S.C. 154(b) by 675 days.

(21) Appl. No.: 10/885,616

(22) Filed: Jul. 8, 2004

(65) Prior Publication Data

US 2006/0008387 A1 Jan. 12, 2006

(51) Int. Cl.
*B01L 3/00* (2006.01)
*G01N 33/00* (2006.01)

(52) U.S. Cl. ........................................ 422/102; 422/73

(58) Field of Classification Search .................. 436/45; 422/100, 922, 73

See application file for complete search history.

(56) References Cited

U.S. PATENT DOCUMENTS 5,830,411 A * 11/1998 Martinell Gisper-Sauch . 422/73
5,972,694 A 10/1999 Mathus .................... 435/288.4
6,235,244 B1 * 5/2001 Allen et al. ................. 422/100
2002/0189374 A1 12/2002 DeSilets et al. .......... 73/864.51

FOREIGN PATENT DOCUMENTS

| | | |
|---|---|---|
| EP | 0 791 394 | 8/1997 |
| EP | 1 547 686 | 6/2005 |
| WO | 03/062508 | 7/2003 |
| WO | 2004/064976 | 8/2004 |

* cited by examiner

*Primary Examiner*—Jill Warden
*Assistant Examiner*—Timothy G Kingan
(74) *Attorney, Agent, or Firm*—Wood, Herron & Evans, LLP

(57) ABSTRACT

A microplate assembly comprising a multi-well microplate and a plurality of reagent wells proximal the multi-wells. The microplate includes a frame that houses a plurality of open wells in a rectangular array. Reagent wells mounted within the microplate to react with the contents of the open wells during a g-force acting upon the microplate. The open wells function as a vessel for liquid samples that occupy predetermined spaces within the interior volumes. Each liquid sample remains within its predetermined space for all orientations of the microplate assembly.

20 Claims, 6 Drawing Sheets

KINETIC MICROPLATE WITH REAGENT WELLS

FIELD OF THE INVENTION

The present invention relates generally to multi-well sample trays which are commonly referred to as microplates and which are used to hold a large number (e.g., 24, 48, 96, or more) of samples in a standardized format to be assayed by various techniques such as autoradiography, liquid scintillation counting (LSC), luminometry, etc. In particular, the present invention relates to a microplate assembly and method which permits a more efficient use of space by adding reagent wells adjacent to the multi-wells.

BACKGROUND OF THE INVENTION

Multi-well microplates play an important role in conventional chemical, biological, pharmacological and related processes that are designed to analyze and/or synthesize large numbers of small fluid samples. Such conventional processes normally employ multi-well microplates as tools when processing, shipping and storing the small liquid samples. Many of these processes achieve high-throughputs by applying modern automation techniques, including robotics. In recent years, efforts have been directed at integrating the different prevailing microplate apparatus into the automation equipment of these high-throughput processes. Such integration efforts, however, have had only limited success. Specifically, spillage, leakage, evaporation loss, airborne contamination and inter-well cross contamination of liquid samples are some of the common deficiencies that limit the application of many standard microplate assemblies in high-throughput systems. Consequently, one of the most critical problems confronting designers of microplate apparatus has been finding techniques of preventing the loss and contamination of well contents without unduly complicating the structures and/or handling requirements of a microplate assembly.

A standard microplate assembly normally comprises a microplate having a plurality of open wells and a an optional closure device for sealing the wells shut. Commonly available microplates generally embody a unitary molded structure comprising a rigid frame for housing a plurality of open wells arranged in a rectangular array. Standard well closures include resilient, press-fit stoppers, rigid screw caps, adhesive films and the like. Microplates come in a range of sizes; a well may be sized to hold as high as five milliliters or as low as only a few microliters of liquid. In addition, microplates come in a variety of materials, such as polystyrene, polycarbonate, polypropylene, TEFLON, glass, ceramics and quartz. Conventional microplates found in many high-throughput systems comprise a ninety-six well geometry molded into an 8 by 12 rectangular array of open circular wells. Microplates with lower well densities (e.g., 24 and 48 wells) and higher well densities (e.g., 384 and 1536 wells) are also available. Nanoliters is a trend for 1536 well plates.

An important microplate application exists in high-throughput organic synthesis (HTOS) systems. HTOS is an important tool for the accelerated synthesis of small organic molecules. HTOS systems employ a variety of automation techniques, which significantly reduce the time required for the development of commercially acceptable compounds in the pharmaceutical, agrochemical and other specialty chemical industries. Most conventional HTOS systems simultaneously synthesize large groups of compounds while using standard microplate assemblies for the reaction, purification and shipment of such compounds. Another important microplate application exists in high-throughput screening (HTS) systems, which examine biological samples for desired properties. HTS systems usually examine the samples while they are contained in the wells of conventional microplates. As such, automatic apparatus must manipulate conventional microplates and their contents during a typical HTS process. Consequently, a primarily requirement of a microplate assembly for use in HTOS and HTS systems is an ability to securely maintain a controlled environment for a liquid sample while the assembly is being manipulated in an automation process. In addition, a microplate assembly must provide means for adding reagents or other materials to an individual well or to multiple wells simultaneously. Some automation devices take some time to add reagents and this could be problematic for an assay requiring all reactions to take place at the same time. Further, a microplate assembly must allow for the mechanical mixing of well contents without risking spills, leaks or cross contamination.

Many HTOS systems deliver multiple samples as solutions of pre-dissolved compounds in microplate assemblies to various locations throughout the world. To prevent a loss of these solutions of pre-dissolved compounds from occurring during delivery, suppliers often convert the solutions into solids prior to shipment by freezing or other methods. Shipping compounds as solids rather than liquids, however, creates problems in dissolution that can complicate and inhibit subsequent sample evaluation procedures. Further, an unstable solid material may disperse on opening of a closed well prior to re-dissolution. Consequently, those skilled in the art have recognized that HTOS systems should preferably deliver solutions of compounds in their stable liquid form.

Accordingly, it is desirable to provide a method and apparatus that delivers reagents or other materials to each individual well or to multiple wells simultaneously and efficiently. There is a need to be able to add reagents simultaneously for all well assays having a time-based, or kinetic character.

SUMMARY OF THE INVENTION

The foregoing needs are met, to a great extent, by the present invention, wherein in one aspect an apparatus is provided that in some embodiments a method and apparatus that delivers reagents or other materials to each individual well or to multiple wells simultaneously and efficiently.

In accordance with one aspect of the present invention, a microplate assembly, comprises a base plate; a plurality of open wells within the base plate; and a plurality of reagent wells proximal the open wells, wherein the open wells are configured in an array and the reagent wells are a predetermined depth and the open wells are a predetermined depth which is greater than the predetermined depth of the reagent wells and the reagent wells further comprises a vertical slit or other opening aligned along the depth of the reagent well and the vertical slit or other opening is disposed in a thin wall common to the open wells, respectively.

In accordance with another aspect of the present invention, a method of microplate processing, comprising the steps of injecting a plurality of open wells within the microplate; injecting a plurality of reagent wells with in the microplate; loading the microplate into a g-force device; and performing centrifugation or other g-inducing method upon the microplate in order to mix the contents of the open wells and the reagent wells. Furthermore, the open wells are configured in an array and the reagent wells are a predetermined depth, wherein the open wells are a predetermined depth which is greater than the predetermined depth of the reagent wells and the reagent wells further comprise a vertical slit or other opening aligned along the depth of the reagent well and the vertical slit or other opening is disposed in a thin wall common to the open wells, respectively. Moreover, the method further comprises the step of simultaneously mixing the contents of the open wells with the contents of the reagent wells.

In accordance with still another aspect of the present invention, a microplate assembly, comprising means for injecting a plurality of open wells within the microplate; means for injecting a plurality of reagent wells with in the microplate; means for loading the microplate into a g-force device; and means for initiating a g-force centrifugation or impact upon the microplate in order to mix the contents of the open wells and the reagent wells, wherein said open wells are configured in an array and the reagent wells are a predetermined depth and the open wells are a predetermined depth which is greater than the predetermined depth of the reagent wells. Furthermore, the reagent wells further comprising a vertical slit or other opening aligned along the depth of the reagent well and the vertical slit or other opening is disposed in a thin wall common to the open wells, respectively. In addition, the microplate assembly further comprises means for simultaneously mixing the contents of the open wells with the contents of the reagent wells.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
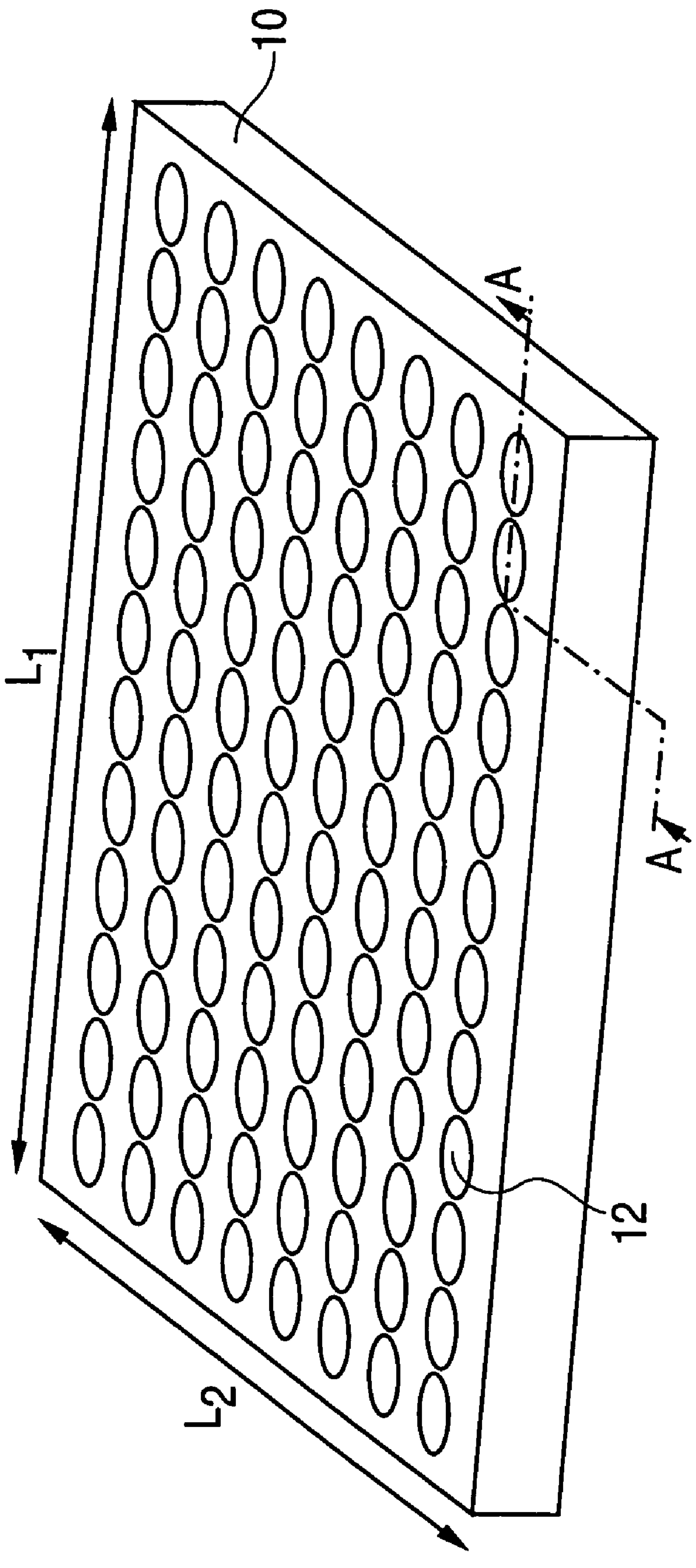
FIG. 1 (PRIOR ART)
FIG. 1 is a perspective view illustrating a conventional microplate.
Figure 2:
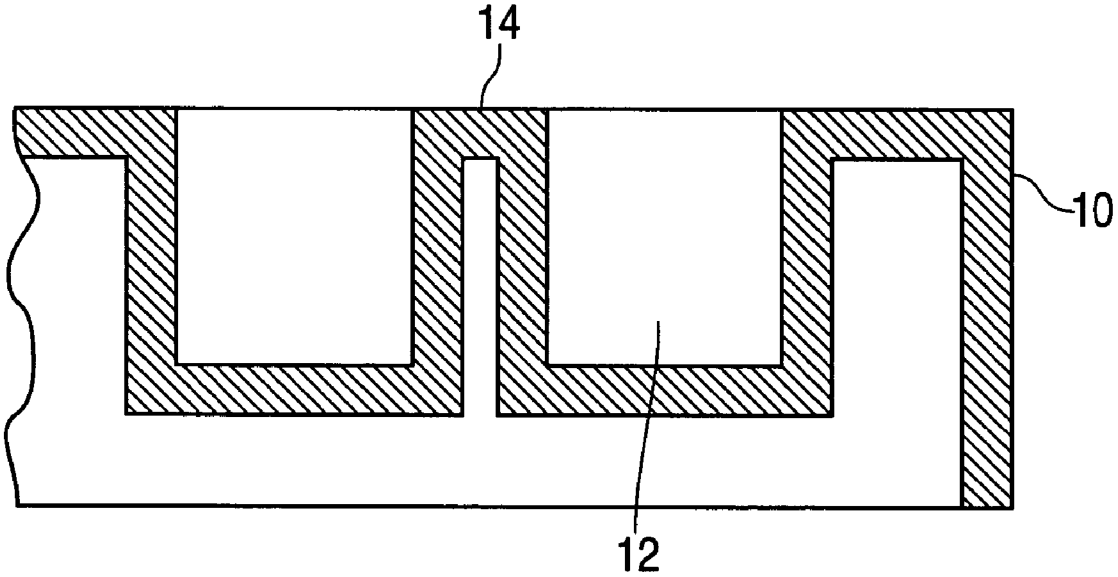
FIG. 2 (PRIOR ART)
FIG. 2 is a cross-sectional view along A-A in FIG. 1 of the wells.
Figure 3:
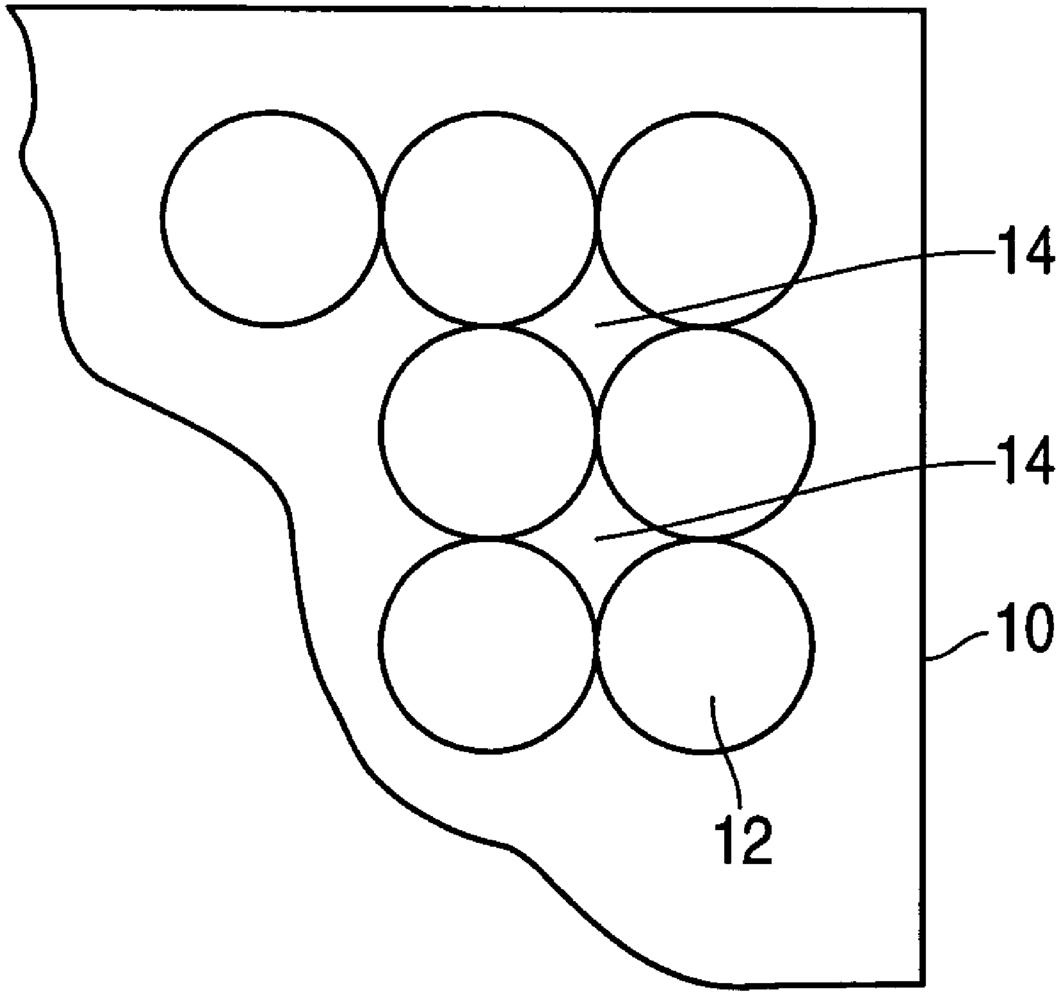
FIG. 3 (PRIOR ART)
FIG. 3 is a cutaway top view of FIG. 1 showing the conventional spacing of the wells.

Referring to FIGS. 1-3, conventional microplates 10 may have ninety-six wells 12 arranged in an eight by twelve grid and may be composed of plastic materials such as polystyrene. Since the wells 12 are typically circular there exists area in the corners of the interstitial spaces 14 between the patterns of circular wells 12 that could be used for placement of liquids used to mix with well 12 contents.

Figure 4:
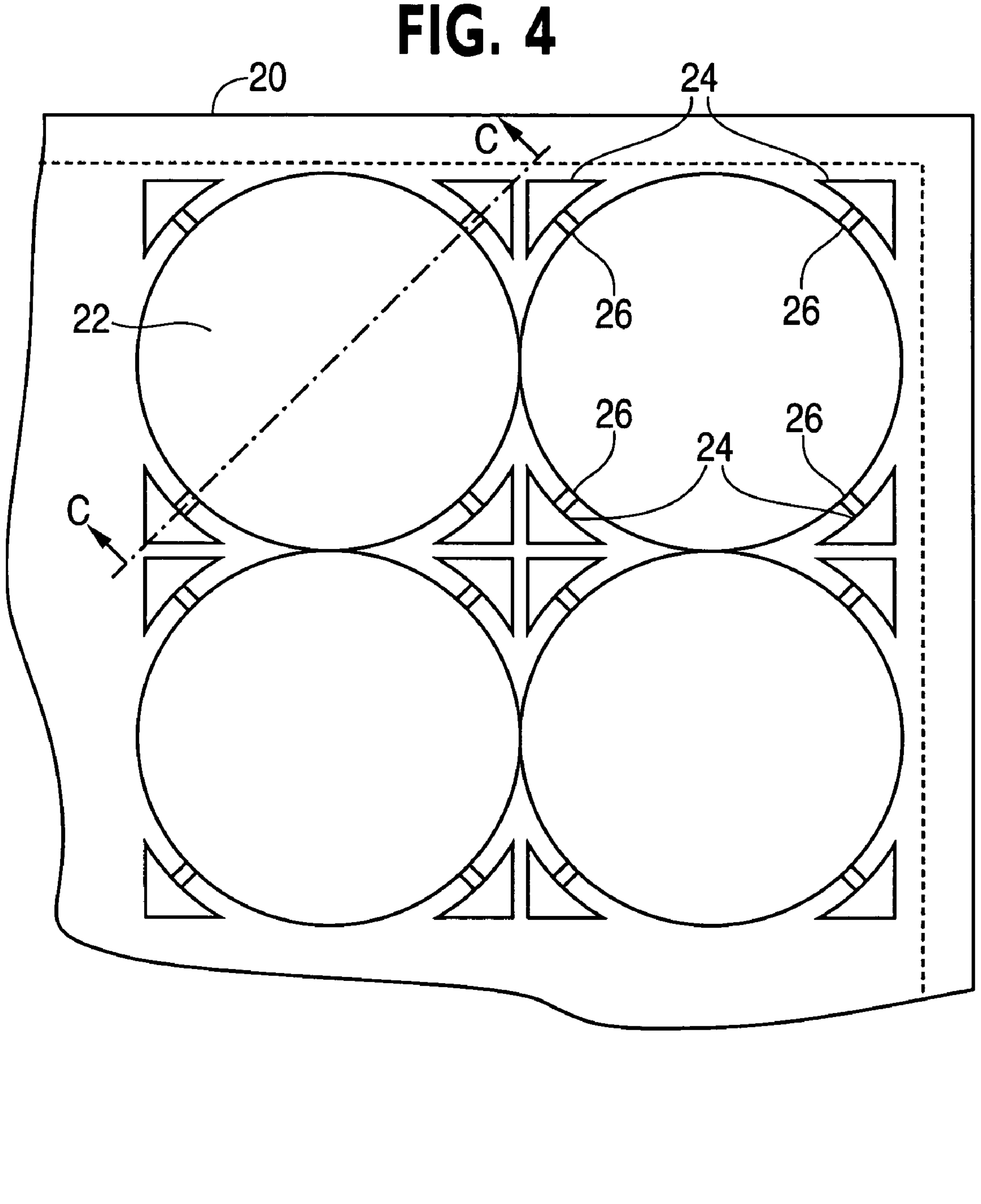
FIG. 4 is a cutaway top view of the present invention showing a plurality of reagent wells.

The invention will now be described with reference to the drawing figures, in which like reference numerals refer to like parts throughout. Referring to FIG. 4, an embodiment in accordance with the present invention provides a microplate 20 with corners areas 14 (shown in FIG. 3) created by the array of circular wells 22 where additional triangular-shaped sectors or wells 24 may be made to hold the kinetic or other reagents. Additionally, these wells or sectors 24 may contain vertical slits or other openings 26 so that under centrifugation all the reagent material passes through or penetrates the vertical slits 26 and flows into the well 22 combining with the original well contents commencing a reaction as desired. Doing so by centrifugation or an impulse force can commence all well reactions simultaneously.

Figure 5:
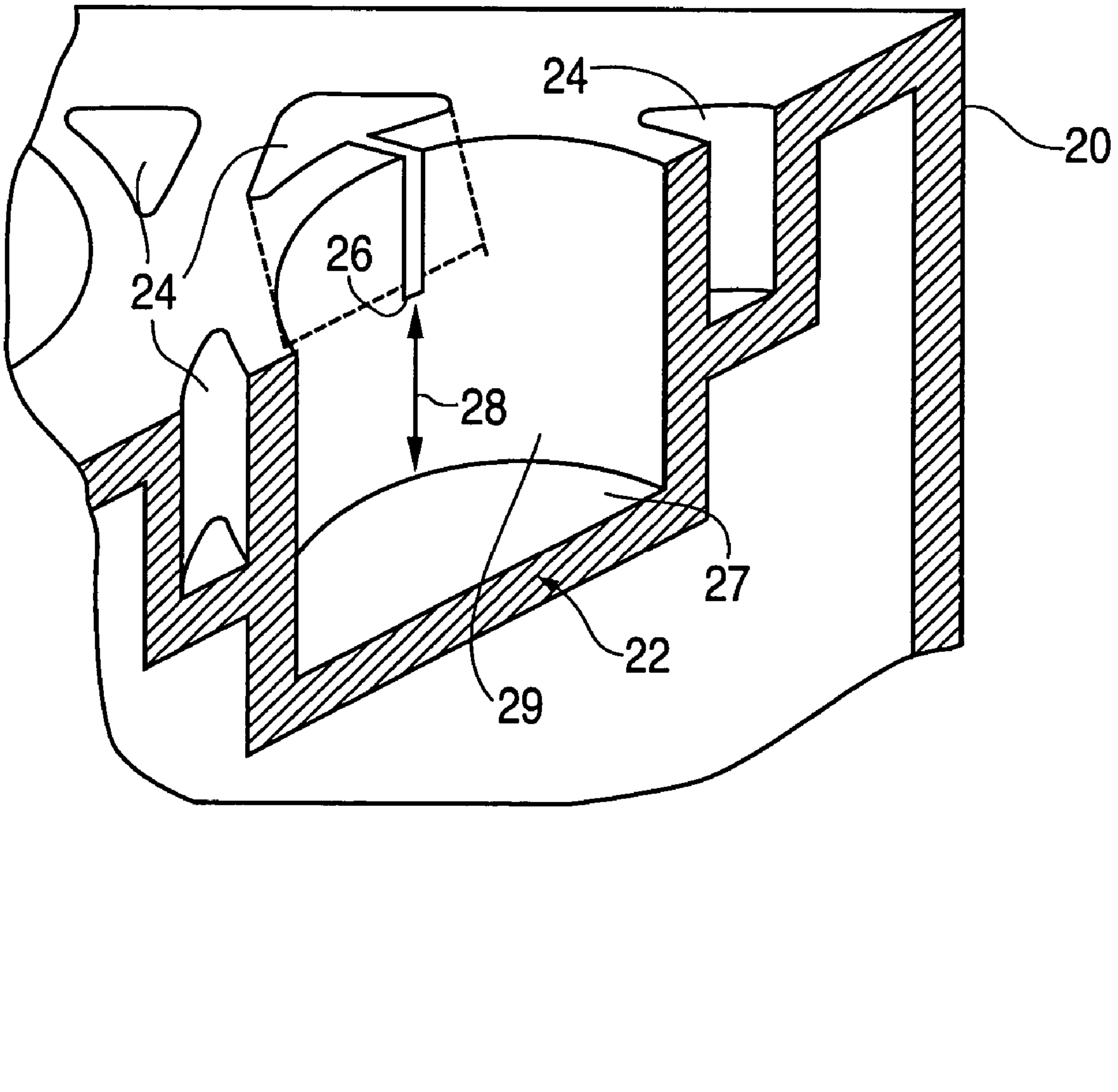
FIG. 5 illustrates an exemplary device of a type suitable for carrying out the functions of an embodiment of the invention taken along C-C in FIG. 4.

Referring to FIG. 5, it should be noted that vertical slits 26 should be disposed at a predetermined height 28 above the well base 27 of the circular wells 22. This predetermined height 28 is dependent on the contents of the circular wells 22 since during centrifugation, the contents of circular wells 22 will create forces against circular well walls 29 which may prevent any reagents placed within sectors 24 from releasing effectively if the slit 26 is disposed too close to the well base 27. The vertical slit 26 may be made by making the wall thin in a vertical section so that the centrifugal force of the reagent may pass through the slit 26 and mix accordingly with the contents of the circular wells 22 simultaneously.

Additionally, different depths of wells can be used for various size liquid additions. Well base 27 may be configured to be conical, concave or as a flat disc as presently shown in FIG. 5

Figure 6:
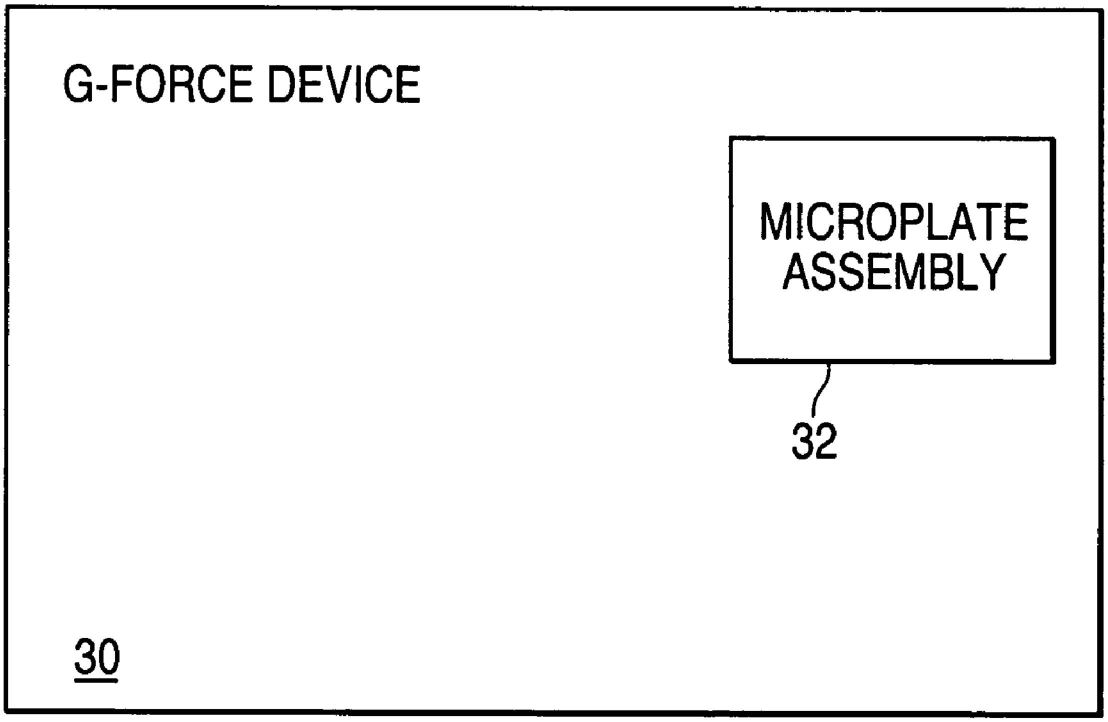
FIG. 6 is a block diagram showing the present invention utilizing a g-force device.

In operation, the microplate 20 will have the circular wells 22 filled or injected with a base element or solution by a known means such as a pipette or the like. The sectors or wells 24 adjacent the circular wells 22 are also filled or injected with the desired reagents for processing by a known means such as a pipette or the like. Now both the circular wells 22 and the sectors 24 could be sealed in order to prevent cross contamination and for movement or shipping. As indicated in FIG. 6, microplate assembly 32 is loaded or placed within a g-force device 30 for processing or mixing of the base element or solution in circular wells 22 and the reagents in sectors 24. The g-force device 30 is operated and the contents of circular wells 22 and sectors 24 are simultaneously mixed or processed. The g-force device 30 may be a centrifuge or other impact or force producing mechanism.

Finally, this method may be used to pre-package reagents in a form whereby the top of the microplate 20 is sealed and microplate 20 is pre-charged with reagents ready to use after the wells 22 are injected with base material or may be pre-loaded with base material.

The thin wall configuration of the present invention may alternatively be configured as a perforated thin breakable seem or a permeable membrane in order to mix the material within the sectors of wells 24 with the material within the circular wells 22 at differing rates. Although an example of the microplate assembly is shown using triangular-shaped wells or sectors 24, it will be appreciated that other wells or sectors 24 of differing shapes and contours can be used. Also, although the microplate assembly is useful to process sample through centrifugation it can also be used to process materials in various states of matter as desired.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A microplate assembly comprising:

a base microplate;

a plurality of open wells within the base plate; and a plurality of reagent wells proximal and between said open wells, with each one of the reagent wells being directly connected to only one open well and being outside the walls of any of the open wells, wherein the open wells are a predetermined depth which is greater than a predetermined depth of the reagent wells, with each one of the open wells including at least four reagent wells at the opposite sides of the open wells being directly connected to each of the open wells.

2. The microplate assembly of claim 1, wherein said open wells are configured in an array with at least two open wells being adjacent and the reagent wells between the open wells including at least two reagent wells being adjacent.

3. The microplate assembly of claim 1, wherein said reagent wells surround the open wells at equidistant spaces.

4. The microplate assembly of claim 1, wherein said reagent wells further comprising a vertical opening aligned along the depth of the reagent well, a portion of each open well being directly connected to a portion of another open well, and a portion of each open well being directly connected to at least one vertical opening of the reagent well, and with no two open wells being directly connected to the same reagent well.

5. The microplate assembly of claim 4, wherein said vertical opening is disposed in a thin wall common to the open wells.

6. The microplate assembly of claim 1, further comprising a top seal configured to cover both the reagent wells and the open wells during shipping.

7. A method of microplate processing, comprising the steps of:

injecting a plurality of reagent wells within the microplate and between each of the plurality of open wells;

loading the microplate into a g-force device; and initiating a g-force upon the microplate in order to mix the contents of the open wells and the reagent wells, wherein the open wells are a predetermined depth which is greater than a predetermined depth of the reagent wells, with each one of the open wells including at least four reagent wells at the opposite sides of the open wells being directly connected to each of the open wells.

8. The method of claim 7, wherein said open wells are configured in an array.

9. The method of claim 7, wherein said reagent wells are a predetermined depth.

10. The method of claim 9, wherein the open wells are a predetermined depth which is greater than the predetermined depth of the reagent wells.

11. The method of claim 7, wherein said reagent wells further comprising a vertical opening aligned along the depth of the reagent well.

12. The method of claim 11, wherein said vertical opening is disposed in a thin wall common to the open wells.

13. The method of claim 7, further comprising the step of simultaneously mixing the contents of the open wells with the contents of the reagent wells.

14. A microplate assembly, comprising:

means for injecting a plurality of open wells within the microplate;

means for injecting a plurality of reagent wells within the microplate, the reagent wells being outside the walls of the open wells and each one of the reagent wells being directly connected to at least one of the open wells;

means for loading the microplate into a g-force device; and means for initiating a g-force upon the microplate in order to mix the contents of the open wells and the reagent wells, wherein the open wells are a predetermined depth which is greater than a predetermined depth of the reagent wells, with each one of the open wells including at least four reagent wells at the opposite sides of the open wells being directly connected to each of the open wells.

15. The microplate assembly of claim 14, wherein said open wells are configured in an array.

16. The microplate assembly of claim 14, wherein said reagent wells are a predetermined depth.

17. The microplate assembly of claim 16, wherein the open wells are a predetermined depth which is greater than the predetermined depth of the reagent wells.

18. The microplate assembly of claim 14, wherein said reagent wells further comprising a vertical opening aligned along the depth of the reagent well.

19. The microplate assembly of claim 17, wherein said vertical opening is disposed in a thin wall common to the open wells.

20. The microplate assembly of claim 14, further comprising means for simultaneously mixing the contents of the open wells with the contents of the reagent wells.

* * * * *

UNITED STATES PATENT AND TRADEMARK OFFICE

CERTIFICATE OF CORRECTION

PATENT NO. : 7,494,623 B2
APPLICATION NO. : 10/885616
DATED : February 24, 2009
INVENTOR(S) : Hugh H. Tansey, III It is certified that error appears in the above-identified patent and that said Letters Patent is hereby corrected as shown below:

On the Title page, Item (57) Abstract, change "Reagent wells mounted within the microplate to react with the contents of the open wells during a g-force acting upon the microplate." to --Reagent wells are mounted within the microplate to react with the contents of the open wells during a g-force acting upon the microplate.--.

In column 1, line 40, change "and a an optional closure device" to --and an optional closure device--.

In column 2, line 7, change "Consequently, a primarily requirement" to --Consequently, a primary requirement--.

In column 2, line 47, change "a microplate assembly, comprises" to --a microplate assembly comprises--.

In column 2, line 53, change "reagent wells further comprises a vertical slit" to --reagent wells further comprise a vertical slit--.

In column 2, line 58, change "a method of microplate processing, comprising the steps of" to --a method of microplate processing comprises the steps of--.

In column 3, line 8, change "a microplate assembly, comprising means for injecting" to --a microplate assembly comprises means for injecting--.

In column 3, lines 18-19, change "the reagent wells further comprising a vertical slit or other opening aligned along the depth of the reagent well and" to --the reagent wells further comprise a vertical slit or other opening aligned along the depth of the reagent well, and--.

In column 4, line 62, change "as a perforated thin breakable seem" to --as a perforated thin breakable seam--.

UNITED STATES PATENT AND TRADEMARK OFFICE

CERTIFICATE OF CORRECTION

PATENT NO. : 7,494,623 B2
APPLICATION NO. : 10/885616
DATED : February 24, 2009
INVENTOR(S) : Hugh H. Tansey, III It is certified that error appears in the above-identified patent and that said Letters Patent is hereby corrected as shown below:

In claim 19, column 6, line 47, change "The microplate assembly of claim 17," to --The microplate assembly of claim 18,--.

Signed and Sealed this

Twenty-third Day of June, 2009

JOHN DOLL
*Acting Director of the United States Patent and Trademark Office*